(12) United States Patent
Ludvig et al.

(10) Patent No.: US 7,885,706 B2
(45) Date of Patent: Feb. 8, 2011

(54) SYSTEM AND DEVICE FOR SEIZURE DETECTION

(75) Inventors: Nandor Ludvig, Richmond Hill, NY (US); Geza Medveczky, Cortlandt Manor, NY (US); Ruben Kuzniecky, Englewood, NJ (US); Gabor Illes, Clifton, NJ (US); Orrin Devinsky, Short Hills, NJ (US)

(73) Assignee: New York University, New York, NY (US)

( * ) Notice: Subject to any disclaimer, the term of this patent is extended or adjusted under 35 U.S.C. 154(b) by 862 days.

(21) Appl. No.: 11/524,160

(22) Filed: Sep. 20, 2006

(65) Prior Publication Data

US 2008/0082019 A1 Apr. 3, 2008
US 2009/0281446 A2 Nov. 12, 2009

(51) Int. Cl.
*A61B 5/0476* (2006.01)

(52) U.S. Cl. .................. 600/544; 600/382; 600/383; 600/393; 600/545

(58) Field of Classification Search .............. 600/378, 600/382, 391, 393, 544, 545; 340/573.1; 128/922, 923
See application file for complete search history.

(56) References Cited

U.S. PATENT DOCUMENTS

| | | | | |
|---|---|---|---|---|
| 5,564,433 A * | 10/1996 | Thornton | ................... | 600/544 |
| 6,148,280 A * | 11/2000 | Kramer | ...................... | 702/153 |
| 6,473,639 B1 * | 10/2002 | Fischell et al. | .............. | 600/544 |
| 7,155,276 B2 * | 12/2006 | Lamont | ...................... | 600/545 |
| 7,277,758 B2 * | 10/2007 | DiLorenzo | ................... | 607/45 |
| 2006/0111644 A1 * | 5/2006 | Guttag et al. | ............... | 600/544 |
| 2007/0287931 A1 * | 12/2007 | Dilorenzo | ................... | 600/545 |
| 2008/0021340 A1 * | 1/2008 | Sarkela | ....................... | 600/544 |

* cited by examiner

*Primary Examiner*—Robert L Nasser
*Assistant Examiner*—Michael D'Angelo
(74) *Attorney, Agent, or Firm*—Fay Kaplun & Marcin, LLP

(57) ABSTRACT

A device comprises a head mounting arrangement sized and shaped to be worn on a user's head and a plurality of electrodes disposed on the arrangement so that, when the arrangement is worn on the user's head, the electrodes contact target portions of a scalp to detect electrical activity of a brain of the user in combination with an image capture device disposed on the arrangement so that, when the arrangement is worn on the user's head, a field of view of the image capture device includes a portion of an anatomy of the user and a processing unit generating EEG data from the electrical activity, wherein, when the EEG data is indicative of an epileptic event, the processing unit activates the image capture device to capture video data of the user and may store the EEG and/or the video data with transmission of warning signals to one or more remote displaying and/or computing arrangements.

22 Claims, 9 Drawing Sheets

SYSTEM AND DEVICE FOR SEIZURE DETECTION

BACKGROUND

Ambulatory epilepsy diagnosis and monitoring systems have been developed to capture epileptic events in non-clinical settings and alleviate the costs associated with long-term, in-patient monitoring sessions conducted in hospitals. The ambulatory system consists of a data acquisition arrangement that captures brain waves of a subject and a video camera mounted on a tripod for capturing video of the subject. The physician may then review the brain waves and the video offline to analyze the subject's activity and any epileptic events that may have occurred during a monitoring period.

The conventional data acquisition arrangement tends to be bulky and heavy, limiting the subject's range of movement and inhibiting performance of daily tasks. That is, the subject may not be able to cook, clean, do laundry or relax comfortably while tethered to the data acquisition arrangement. Additionally, the video camera is statically positioned and captures only a limited viewing range. If the subject is outside of the viewing range or if the video camera is otherwise non-functional (out of tape, battery dead, etc.), the subject's activity and the epileptic event(s) will not be captured. Thus, the conventional ambulatory systems severely restrict the subject's activity and movement even in non-clinical settings.

SUMMARY OF THE INVENTION

The present invention relates to a seizure detector headset comprising a head mounting arrangement sized and shaped to be worn on a user's head and a plurality of electrodes disposed on the arrangement so that, when the arrangement is worn on the user's head, the electrodes contact target portions of a scalp to detect electrical activity of a brain of the user in combination with an image capture device disposed on the arrangement so that, when the arrangement is worn on the user's head, a field of view of the image capture device includes a portion of an anatomy of the user and a processing unit generating EEG data from the electrical activity, wherein, when the EEG data is indicative of an epileptic event, the processing unit activates the image capture device to capture video data of the user.

DETAILED DESCRIPTION

Figure 1:
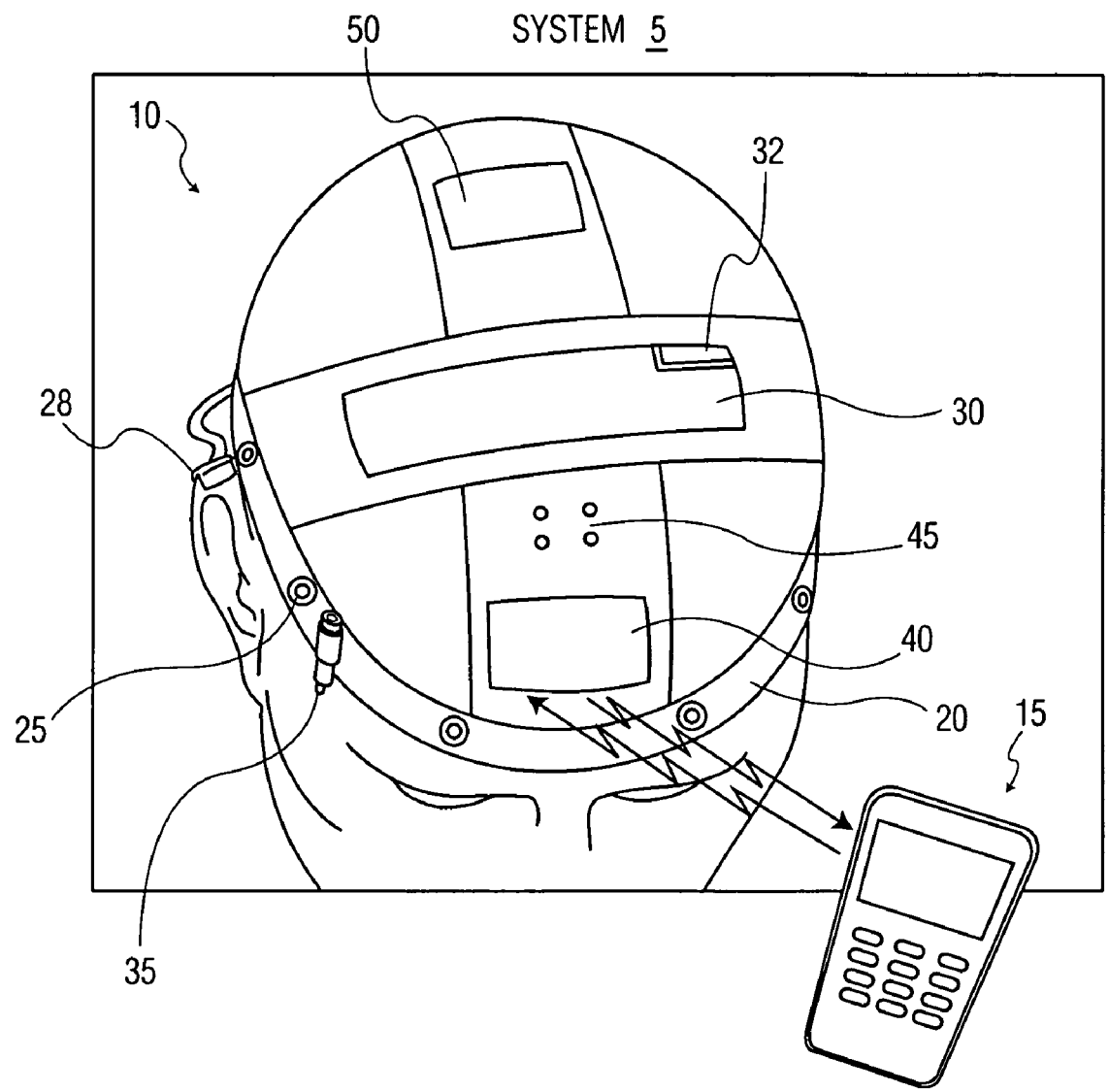
FIG. 1 shows an exemplary embodiment of a wearable EEG system according to the present invention.

The present invention may be further understood with reference to the following description and the appended drawings, wherein like elements are provided with the same reference numerals. The present invention relates to a system and device for seizure detection. The exemplary embodiments of the present invention provide a seizure detector headset which comprises a wearable electroencephalogram (EEG) system that monitors and processes EEG signals of a subject to detect an epileptic event, provide visual evidence of the epileptic event and alert caregivers and/or medical/emergency personnel that the epileptic event is occurring. Additionally, the EEG signals produced before, during and after the epileptic event may be recorded and analyzed to diagnose (or revise a diagnosis of) the subject and/or prescribe a treatment protocol. The "epileptic event" as used herein refers to any brain activity indicative of a seizure or seizure-related symptom, any brain activity indicative of the onset of a seizure and/or any brain activity indicating that a seizure is likely to occur in the near future (i.e., within a predetermined time period). The predetermined time period is preferably measured in minutes.

FIG. 1 shows an exemplary embodiment of a wearable EEG system 5 according to the present invention. The system 5 may be embodied as a seizure detector headset which comprises a wearable EEG arrangement 10 communicatively linked to a computing device 15. The wearable EEG arrangement 10 includes a headband 20 (or cap) that is sized and shaped to be mounted/worn on the head (or scalp) as shown in FIG. 1. Preferably, the headband 20 is adjustable (e.g., mechanically, elastic, etc.) so that the wearable EEG arrangement 10 may be used on multiple subjects and allow a particular subject to rent/lease the wearable EEG system 5 for diagnostic intervals. However, those of skill in the art will understand that the headband 20 may be fitted to the particular subject when, for example, the subject is required by a physician to utilize the system 5 at all times.

A plurality of EEG electrodes 25 may be affixed to predetermined locations on the headband 20 so that when the headband 20 is worn, the EEG electrodes 25 are disposed in corresponding locations on the scalp. In a preferred embodiment, the headband 20 includes eight EEG electrodes 25 and two reference electrodes 28 which are attached to, for example, the ears. One exemplary electrode configuration comprises FP1, F7, C3 and P7 active electrodes on the left hemisphere and FP2, F8, C4 and P8 active electrodes on the right hemisphere. Of course, any other electrode configuration can readily be arranged. When the headband 20 is worn, the EEG electrodes 25 come in contact with the scalp to detect neurophysiological activity by measuring an intensity and pattern of electrical signals generated by the brain. Spontaneous oscillations in the electrical signals are typically referred to as brain waves or EEG. The EEG is a record derived from the spontaneously oscillating electrical signals and other electrical activity (e.g., "noise" or electrical activity of a non-cerebral origin). As understood by those of skill in the art, the number and configuration of the EEG electrodes 25 and the reference electrodes 28 may depend upon, for example, the subject's medical history, a diagnostic task, etc.

The electrical signals detected by the EEG electrodes 25 and the reference electrodes 28 may be output to a processing unit 30 for analysis. In the exemplary embodiment, the processing unit 30 is disposed on a cross-band of the headband 20 which runs transversely over the scalp. However, those of skill in the art will understand that the processing unit 30 may be disposed anywhere on the headband 20. The processing unit 30 may amplify, filter and/or digitize the electrical signals and determine whether the electrical signals are indicative of a target brain activity such as an epileptic event. When an epileptic event is detected, the processing unit 30 may activate components of the system 5, transmit a warning signal(s) to one or more remote computing arrangements (e.g., the computing device 15, a server, etc.) and save EEG data corresponding to the electrical signals on a storage device (e.g., a removable memory card 32 coupled to the processing unit 30, a remote database, etc.). Operation of the processing unit 30 will be explained further below.

In the exemplary embodiment, the headband 20 also includes an image capture device (e.g., a video camera 35, a digital camera). When the headband 20 is worn, the video camera 35 is preferably focused downward so that an imaging field of the video camera 35 includes of the subject's trunk, hands and feet. The video camera 35 may be statically positioned on the headband 20 or moveable and/or rotatable relative thereto. In addition, there may be more than one video camera disposed on the headband 20. Because the video camera 35 is disposed on the headband 20, it is preferable that the video camera 35, as well as the other components of the wearable EEG arrangement 10, are lightweight and disposed in positions to balance any load imparted to the head.

The headband 20 may further include a radio frequency transceiver 40 for conducting wireless communications, an indicator (e.g., LEDs 45, speaker, etc.) for providing visual (or audible) signals (e.g., indicating that an epileptic event has been detected), and a battery 50 providing power to the components of the wearable EEG arrangement 10. The transceiver 40 may allow the processing unit 30 to, for example, exchange data, including the EEG data, warning signals and instructions with the computing device 15. The LEDs 45 may be activated upon detection of an epileptic event. Upon noticing activation of the LEDs 45, a nurse, physician or the subject may administer anti-epileptic medication to prevent the occurrence of the epileptic event or reduce the severity thereof. The battery 50 may be a rechargeable battery (e.g., Li ion) or single-use/alkaline which has, for example, a voltage of 3.6V and provides a current of 1000 mA.

As noted above, the system 5 may also include the computing device 15 which is communicatively linked to the wearable EEG arrangement 10. The computing device 15 may be any processor-based device including, but not limited to, a mobile phone, a PDA, a laptop, a tablet computer, a handheld computer, a PC or any of a number of computers accessed via a network such as the Internet, a WLAN, etc. In other exemplary embodiments, the computing device 15 may simply be a display arrangement such as, for example an LCD display screen or CRT. As will be explained further below, the computing device 15 may be used to monitor EEG data, receive warning signals when an epileptic event is detected, activate the wearable EEG arrangement 10, etc. The computing device 15 may be further utilized to review the EEG data obtained by from the EEG electrodes 25 and video data captured by the video camera 35 to diagnose the subject, update a previous diagnosis of the subject, prescribe/update a treatment protocol, etc.

Figure 3A:
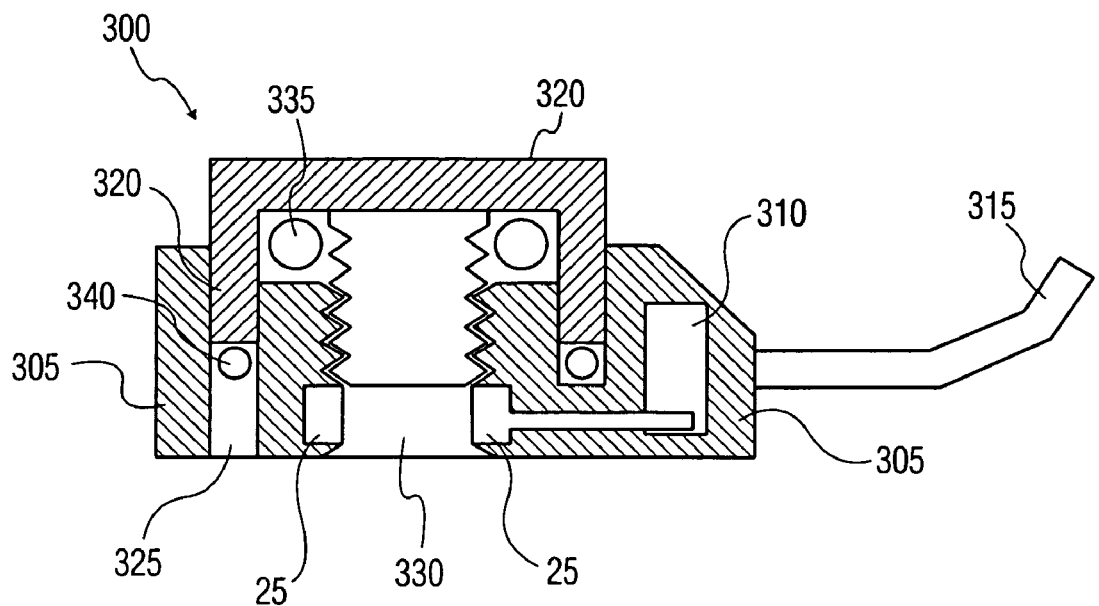
FIG. 3a shows a cross-sectional view of an exemplary embodiment of an EEG electrode unit according to the present invention.
Figure 3B:
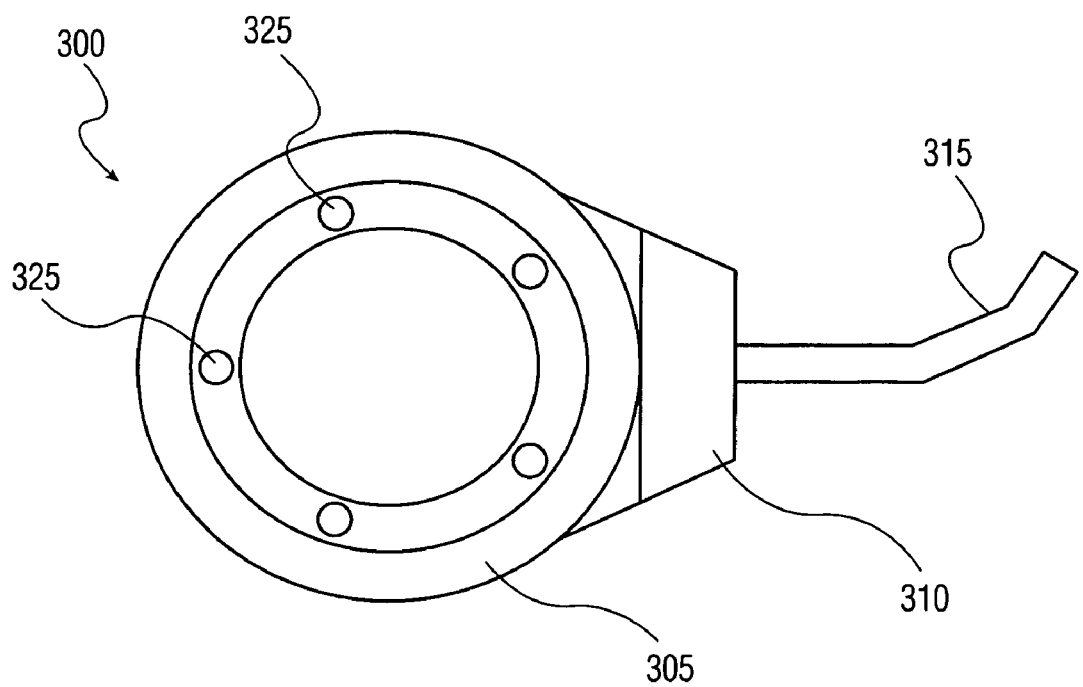
FIG. 3b shows an underside view of an exemplary embodiment of an EEG electrode unit according to the present invention.

In an exemplary use of the system 5, the wearable EEG arrangement 10 is placed on the head. The reference electrodes 28 are attached to the ears and the EEG electrodes 25 are placed in contact with the scalp. FIGS. 3*a-b* show an exemplary embodiment of an EEG electrode unit 300 which includes one of the EEG electrodes 25 and facilitates attachment of the EEG electrode 25 to the scalp, ensuring that substantially noise- and artifact-free EEG electrical signals are harvested. Each of the EEG electrodes 25 utilized by the wearable EEG arrangement 10 may be included in a respective EEG electrode unit 300. Thus, a plurality of EEG electrode units 300 may be disposed on the headband 20.

The EEG electrode unit 300 comprises a housing 305 which holds the EEG electrode 25 and an operational amplifier 310 coupled thereto. An output of the operational amplifier 310 is coupled to a cable 315 which leads to the processing unit 30. In the exemplary embodiment, the housing 305 may be substantially cylindrical with an open bottom portion and a threaded upper portion. The EEG electrode 25 may fit within the open bottom portion so that a detecting face of the EEG electrode 25 contacts the skin when the headband 20 is worn. A threaded plug 320 mates with the threaded upper portion of the housing 305. As shown in FIG. 3*a*, rotation of the plug 320 expunges adhesive from one or more channels 325 formed within the housing 305 so that the adhesive exits the channels 325 seeping between the bottom portion of the housing 305 and the skin to form a temporary bond therebetween. Additionally, as the plug 320 is rotated, conductive paste may be expunged from a central channel 330, seeping between the EEG electrode 25 and the skin to form an electrically conductive bond therebetween. A visual indicator (e.g., green-to-red color change) on the plug 320 may indicate that all of the adhesive and/or conductive paste has been expunged from the EEG electrode unit 300.

As shown in FIG. 3*a*, an upper portion of the central channel 330 has threads (or other connectors) mating with threads on a central member formed on an underside of the plug 320. An O-ring 335 disposed circumferentially around the central member prevents backflow of the conductive paste while stoppers 340 in the channels 325 prevent back flow of the adhesive. Between uses the EEG electrode units 300 may be disposable or reloaded with the adhesive and the conductive paste.

Those of skill in the art will understand that variations may be made to the exemplary embodiments of the EEG electrode units 300 described above without departing from their overall purpose. For example, the plug 320 may utilize a plunging action (syringe-like) to expunge the adhesive and paste. Also, the EEG electrode units 300 may not include the adhesive and/or paste, which may be applied by a nurse or physician. In addition, the operational amplifier 310 may be included as part of the processing unit 30 or otherwise separated from the housing 305. Alternatively, the signals from the EEG electrode units 300 may be transmitted wirelessly to the processing unit as would be understood by those of skill in the art.

Referring back to the exemplary use of the system 5, the headband 20 is placed on the scalp and the EEG electrodes 25 are aligned in their proper positions on the scalp. For example, the headband 20 may have a marker (e.g., center of the forehead) which allows the subject to align the EEG electrodes 25 in their proper positions. After the EEG electrodes 25 have been properly aligned, the plugs 320 of the EEG electrode units 300 are rotated to apply the adhesive and the conductive paste to the scalp fixing the EEG electrode units 300 to the target locations and electrically coupling the EEG electrodes 25 to the scalp.

When the EEG electrodes 25 have been secured to the scalp, the wearable EEG arrangement 10 may be powered. In one exemplary embodiment, a switch is provided on the wearable arrangement EEG arrangement 10 which activates the processing unit 30. In another exemplary embodiment, the processing unit 30 may receive a wireless activation signal from the computing device 15 via the transceiver 40. When the processing unit 30 is activated, the EEG electrodes 25, the video camera 35, and/or the LEDs 45 may be initialized. For example, the processing unit 30 may harvest EEG data from the EEG electrodes 25 and/or the video data from the video camera 35, and/or flash the LEDs 45. Segments (e.g., 20 sec) of EEG data and/or the video data may be transmitted to the computing device 15 for display thereon. If the processing unit 30 does not detect an epileptic event, the computing device 15 transmits a monitoring initiation signal to the processing unit 30 via the transceiver 40 instructing the processing unit 30 to being its monitoring and response program.

In the exemplary embodiment, the monitoring and response program utilized by the processing unit 30 is preferably a vector-analysis-based application as described in Kovacs L, Ludvig N., Devinsky O., Kuzniekcy R. I., "Vector-analysis: Low-power-requiring software for real-time EEG seizure recognition/prediction in hybrid neuroprosthetic devices," Epilepsia 46 (Suppl. 8) 317-318 (2005) and U.S. patent application Ser. No. 11/224,661 entitled "Apparatus and Method for Monitoring and Treatment of Brain Disorders," the entire disclosures of which are expressly incorporated herein by reference. The processing unit 30 may monitor the EEG data provided by the EEG electrodes 25 to detect for an epileptic event. Alternatively, any other EEG-seizure recognition software may be employed. However, this may increase the bulk of the system as the power required for other types of software may be greater.

Figure 2:
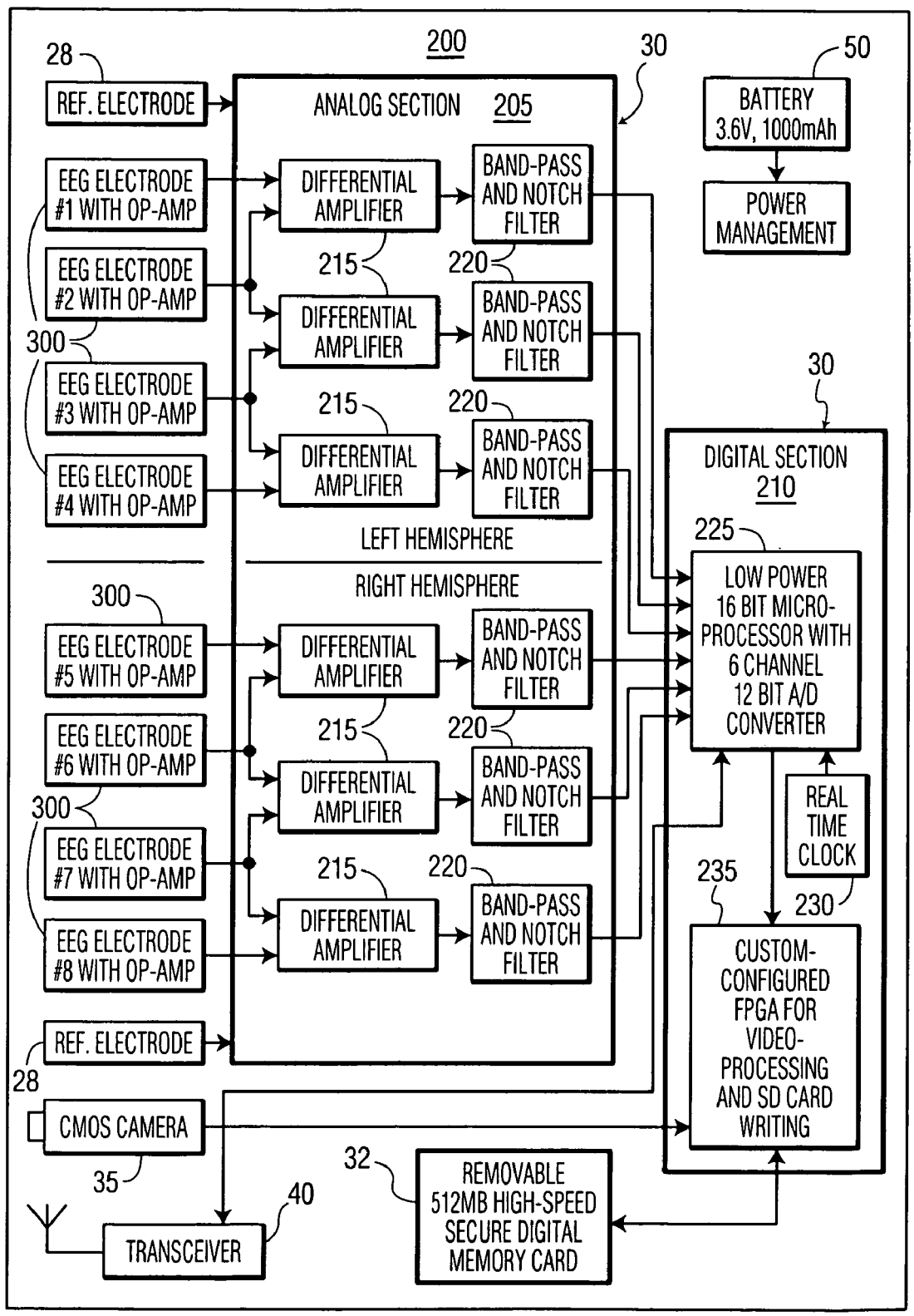
FIG. 2 shows an exemplary embodiment of an architecture of a wearable EEG arrangement according to the present invention.

FIG. 2 shows an exemplary embodiment of an architecture 200 of the wearable EEG arrangement 10 according to the present invention. The EEG electrode units 300 and the reference electrodes 28 are electrically coupled to inputs of the processing unit 30. In this manner, the brain waves are detected and converted into electrical signals by the EEG electrodes 25. The electrical signals detected by each EEG electrode 25 are passed through a corresponding operational amplifier 310 in the EEG electrode unit 300 to reduce and/or eliminate movement artifacts from the electrical signals. The operational amplifier 310 may be directly coupled to the EEG electrode 25. The artifact-free electrical signals are then output to the processing unit 30.

The exemplary processing unit 30 comprises an analog section 205 which receives electrical signals from the EEG electrode units 300 and a digital section 210 which digitizes and analyzes output from the analog section 205 to detect epileptic events. As shown in FIG. 2, the analog section 205 may include a series of amplifiers 215 (e.g., differential amplifiers) and filters (e.g., band-pass and notch filters 220) for amplifying and filtering the electrical signals from the EEG electrode units 300. The analog section 205 may output segments of the electrical signals which are useful in the analysis of epileptic events. The band-pass filters may be preset to a band-pass of 0.5-35 Hz for indicating an ongoing seizure, or to a band-pass of 0.5-200 Hz to indicate both an ongoing seizure and the imminent development of a seizure.

The output of the analog section 205 is passed to the digital section 210 and, in particular, a microprocessor 225 with an analog-to-digital (ADC) converter to digitize the segments of the electrical signals and generate digital EEG data. The digital section 210 may further include a real time clock 230 for time-stamping the EEG data and a field-programmable gate array (FPGA) 235 for controlling and obtaining video data from the video camera 35 and writing the EEG data and/or the video data to the memory card 32. In the exemplary embodiment, the memory card 32 may be a 512 MB high-speed Secure Digital (SD) memory card, but those of skill in the art will understand that other removable memory arrangements may be used with the wearable memory arrangement 10, e.g., a CF card, a PCMCIA card, a memory stick, a USB device, a MMC card, an xD-picture card, a smartmedia card, etc. Those of skill in the art will understand that a non-removable may also be utilized.

The digital section 210 may further include a memory (not shown) storing reference data corresponding to EEG data indicative of epileptic events. The reference data may include previous EEG data recorded from the subject or from a group of subjects during one or more epileptic events. Alternatively, the reference data may be a function or other representation which has been constructed based on such EEG data. Alternatively, the memory card 32 may store the reference data tailored for use by a particular subject. In a further embodiment, the computing device 15 may store or have access to the reference data. In this embodiment, the computing device 15, rather than the processing unit 30, may detect the occurrence of epileptic events.

In the exemplary embodiment, the microprocessor 225 analyzes the EEG data to detect epileptic events. That is, the EEG data is compared to the reference data to determine whether the subject is experiencing an epileptic event. If the EEG data is not indicative of an epileptic event, the EEG data may be discarded after a predetermined time. For example, a delay may be used so that the EEG data recorded previous to an epileptic event may be reviewed. Alternatively, all (or selected portions) of the EEG data may be stored on the memory card 32 and/or transmitted to the computing device 15 for long-term analysis.

When the EEG data is indicative of an epileptic event, the processing unit 30 may write the EEG data to the memory card 32 for a predetermined duration (e.g., about 10-30 seconds). Alternatively, the predetermined duration may be selected to correspond to a duration of the epileptic event, i.e., the predetermined time equals the time during which the EEG data is indicative of an ongoing epileptic event. In another exemplary embodiment, the processing unit 30 may continue to write EEG data to the memory card 32 for a predetermined time after cessation of the epileptic event. In this embodiment, anti-epileptic drugs or other seizure treatments may be evaluated for their ability to quell the seizure and/or return the subject to a normal EEG. In other exemplary embodiments, the EEG data may be downloaded (e.g., batch, streamed) to the computing device 15 when the processing unit 30 detects the epileptic event or onset thereof. Thus, a nurse, physician or other caregiver may monitor the EEG data to determine the severity of epileptic events, a proper treatment, etc.

Figure 4:
FIG. 4 shows an exemplary embodiment of video data captured by a wearable EEG arrangement according to the present invention.

Upon detecting an epileptic event, the processing unit 30 preferably also activates the video camera 35. As shown in FIG. 4, the video camera 35 captures video data during the epileptic event. The processing unit 30 may then write the video data to the memory card 32 or download this data to the computing device 15. The video camera 35 is preferably activated for so long as the EEG data is recorded. Thus, video of the epileptic event may be analyzed in conjunction with the EEG data that was exhibited during the epileptic event. Those skilled in the art will understand that, if memory capacity is sufficient, the video and EEG data may be continuously recorded for later analysis with portions indicative of ongoing to imminent seizure activity flagged.

When an epileptic event has been detected, the processing unit 30 may also transmit a warning signal and/or activate the LEDs 45. The warning signal may be a wireless signal transmitted to the computing device 15. Alternatively, the warning signal may be a broadcast signal so that any wireless computing device in range of the transceiver 40 may detect and respond to the warning signal. The warning signal may include data which, for example, identifies the subject (e.g., name, age, etc.), includes medical history data (e.g., diagnosis, treatments, severity, etc.), identifies a location of the subject, etc.

After the EEG data and the video data have been written to the memory card 32, the memory card 32 may be removed from the wearable EEG arrangement 10 and coupled to the computing device 15. The EEG data and the video data may then be stored in a database and/or analyzed to determined/update a diagnosis of the subject, prescribe a treatment protocol, etc. Of course, as described above, this data may be transmitted wirelessly to the computing device 15 or via a cabled connection without removing the memory card 32.

Figure 5:
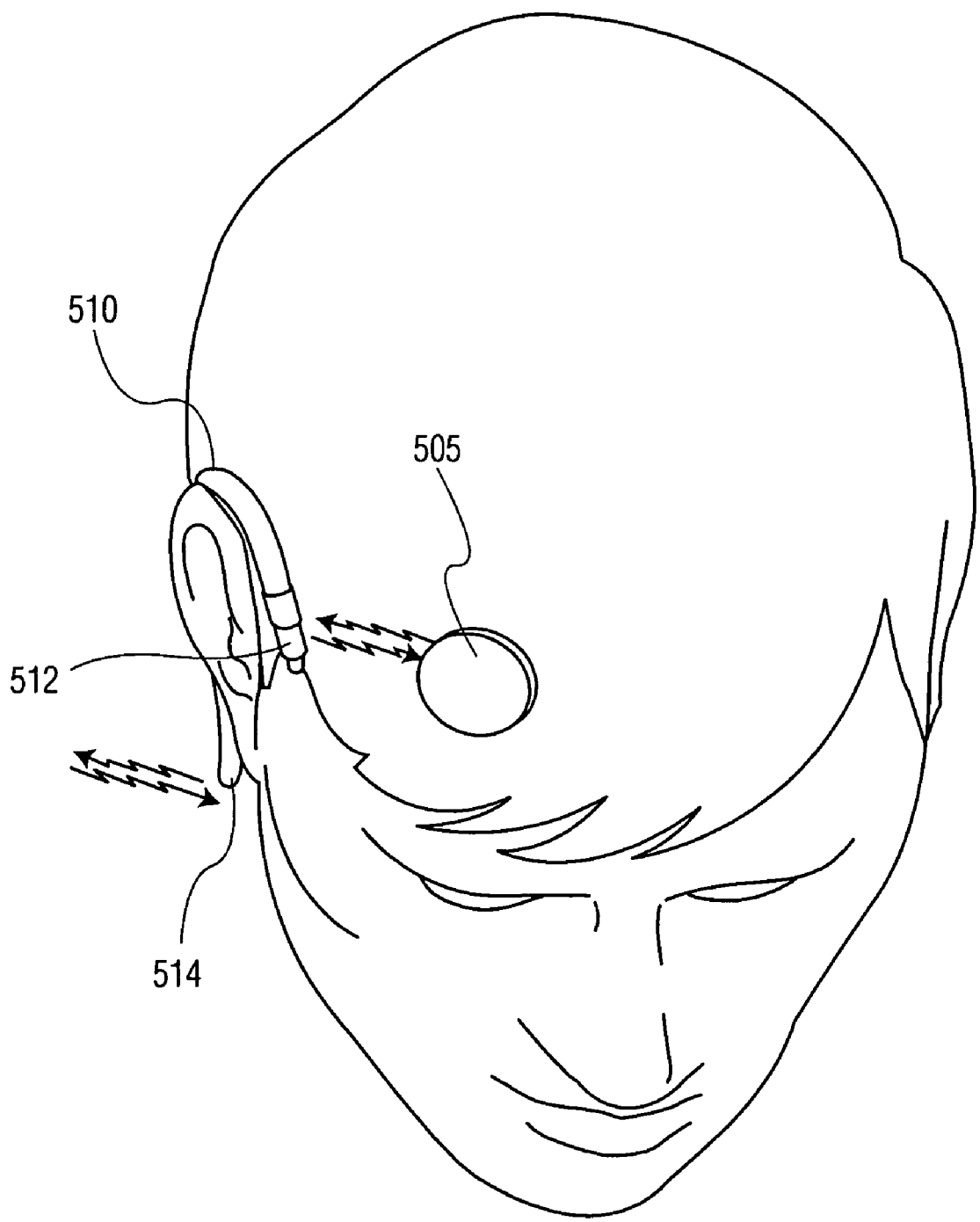
FIG. 5 shows an alternative exemplary embodiment of a wearable EEG system according to the present invention.

FIG. 5 shows another exemplary embodiment of a wearable EEG system 500 according to the present invention. The wearable EEG system 500 includes a wearable EEG arrangement (e.g., an EEG minidisc 505) and an image capture device (e.g., a video camera unit 510). In this exemplary embodiment, the wearable EEG system 500 preferably includes only a single EEG minidisc 505 which performs EEG data acquisition, data analysis and signaling functions while the video camera unit 510 is a separately wearable device which includes a video camera 512 and a transceiver 514 for wirelessly communicating with the EEG minidisc 505. However, those of skill in the art will understand that the number of EEG minidiscs 505 may vary as desired/prescribed, and that the EEG minidisc 505 may be physically coupled to the video camera 510, in which case the video camera 510 may not require the transceiver 514.

As shown in FIGS. 6a-d, an EEG minidisc 505 according to an exemplary embodiment of the present invention includes a housing 515 with two EEG electrodes 520 disposed on a bottom surface thereof. A channel 525 extending through the housing 515 from a top surface to the bottom surface allows the conductive paste to be applied to a bottom surface of the EEG electrodes 520. The adhesive for securing the EEG minidisc 505 to the scalp may also be applied through the channel 525, through other channels or directly to the scalp and/or to the bottom surface of the housing 515.

Figure 6A:
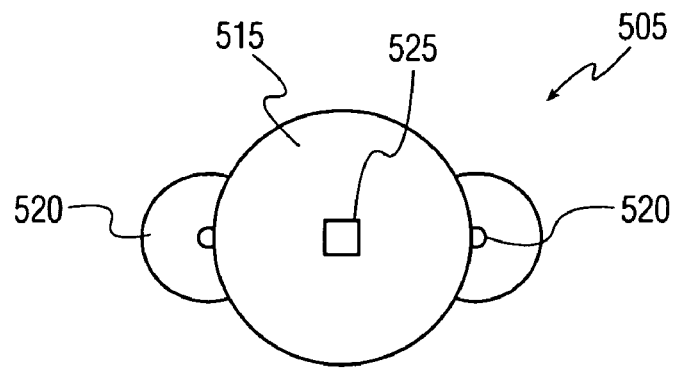
FIG. 6a shows a top view of an exemplary embodiment of an EEG minidisc according to the present invention.
Figure 6B:
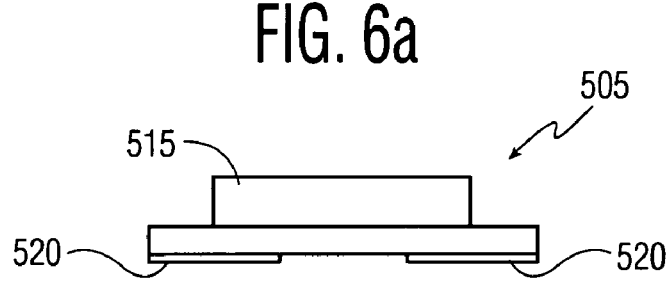
FIG. 6b shows a side view of an exemplary embodiment of an EEG minidisc according to the present invention.
Figure 6C:
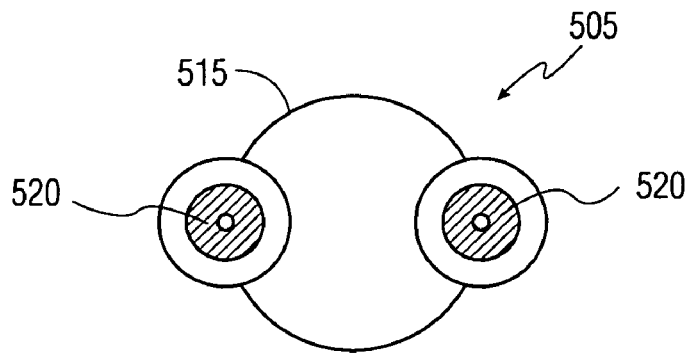
FIG. 6c shows a bottom view of an exemplary embodiment of an EEG minidisc according to the present invention.
Figure 6D:
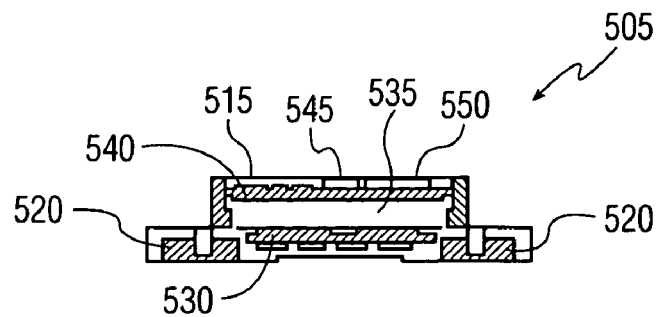
FIG. 6d shows a cross-sectional view of an exemplary embodiment of an EEG minidisc according to the present invention.

As shown in FIG. 6d, a processing unit 530 included in the housing 515 of the EEG minidisc 505 may include one or more amplifiers and filters, in addition to a microprocessor. The processing unit 530 may perform functions similar to those performed by the processing unit 30 described above. That is, the electrical signals obtained by the EEG electrodes 520 may be amplified, filtered (e.g., digital post-filtering) and digitized to generate the digital EEG data, and the EEG data may be analyzed by the microprocessor to detect the occurrence of an epileptic event or the imminent onset thereof, at which time the EEG minidisc 505 may activate the video camera 512. The processing unit 530 may also transfer the EEG data to a memory on the EEG minidisc 505 and/or transmit the EEG data as a wireless signal (e.g., optical, RF) to a remote computing device.

The EEG minidisc 505 may further include a battery 535, a battery charging circuit 540, an optical transceiver 545 and an RF transceiver 550. The battery charging circuit 540 may be, for example, a magnetic coupling circuit which may be coupled to a charger/data reader to be charged and exchange data with a computing device, as will be described further below. The optical transceiver 545 may be used to exchange data with the computing device, and the RF transceiver 550 may transmit signals to the receiver 514 on the video camera unit 510. The EEG minidisc 505 may further include an indicator (e.g., LED, speaker, etc.) which is activated upon detection of an occurring or imminent epileptic event.

Figure 7:
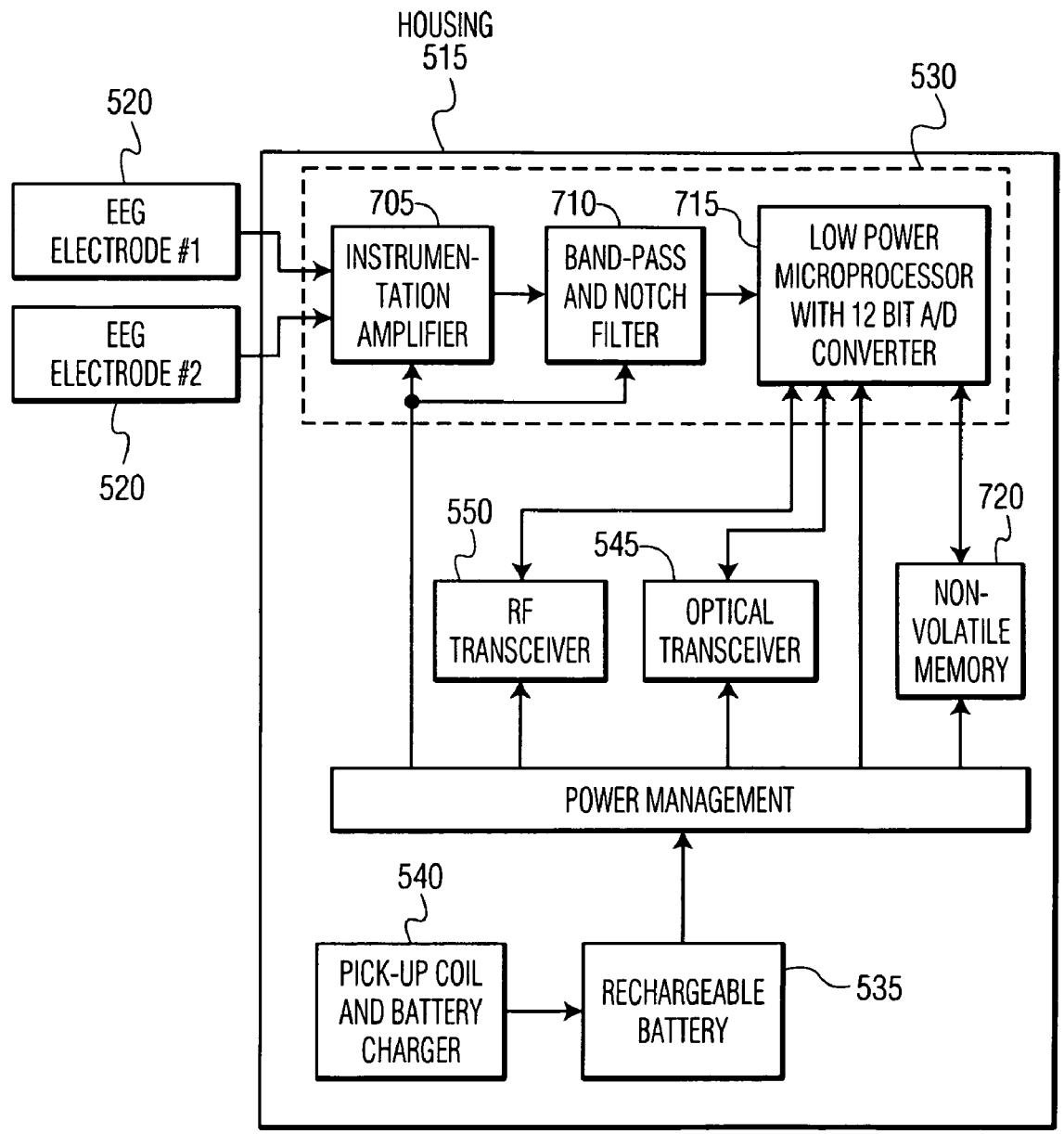
FIG. 7 shows an exemplary embodiment of an architecture of an EEG minidisc according to the present invention.

FIG. 7 shows an exemplary embodiment of an architecture of the EEG minidisc 505 according to the present invention. The EEG electrodes 520 are coupled to the housing 515 and pass, to the processing unit 530, electrical signals corresponding to detected brain waves. Within the processing unit 530, the electrical signals are amplified by an amplifier 705 (e.g., an instrumentation amplifier), filtered by a filter 710 (e.g., a band-pass and notch filter) and digitized and processed by a microprocessor 715 (e.g., a low-power micro with a 12 bit ADC) to generate digital EEG data. The microprocessor 715 may then compare the EEG data to reference data stored in a memory 720 (e.g., a non-volatile memory) in the EEG minidisc 505 to determine the occurrence or likelihood of occurrence in the near future of an epileptic event or onset thereof. When an epileptic event is detected, the microprocessor 715 may transmit an activation signal via the transceiver 550 to the receiver 514 on the video camera unit 510, activating the video camera 512. The transceiver 550 may also be used to transmit a warning signal upon detection of the epileptic event. The EEG minidisc 505 may also incorporate an optical transceiver 545 to receive optical activation signals from an optical transmitter.

Figure 8:
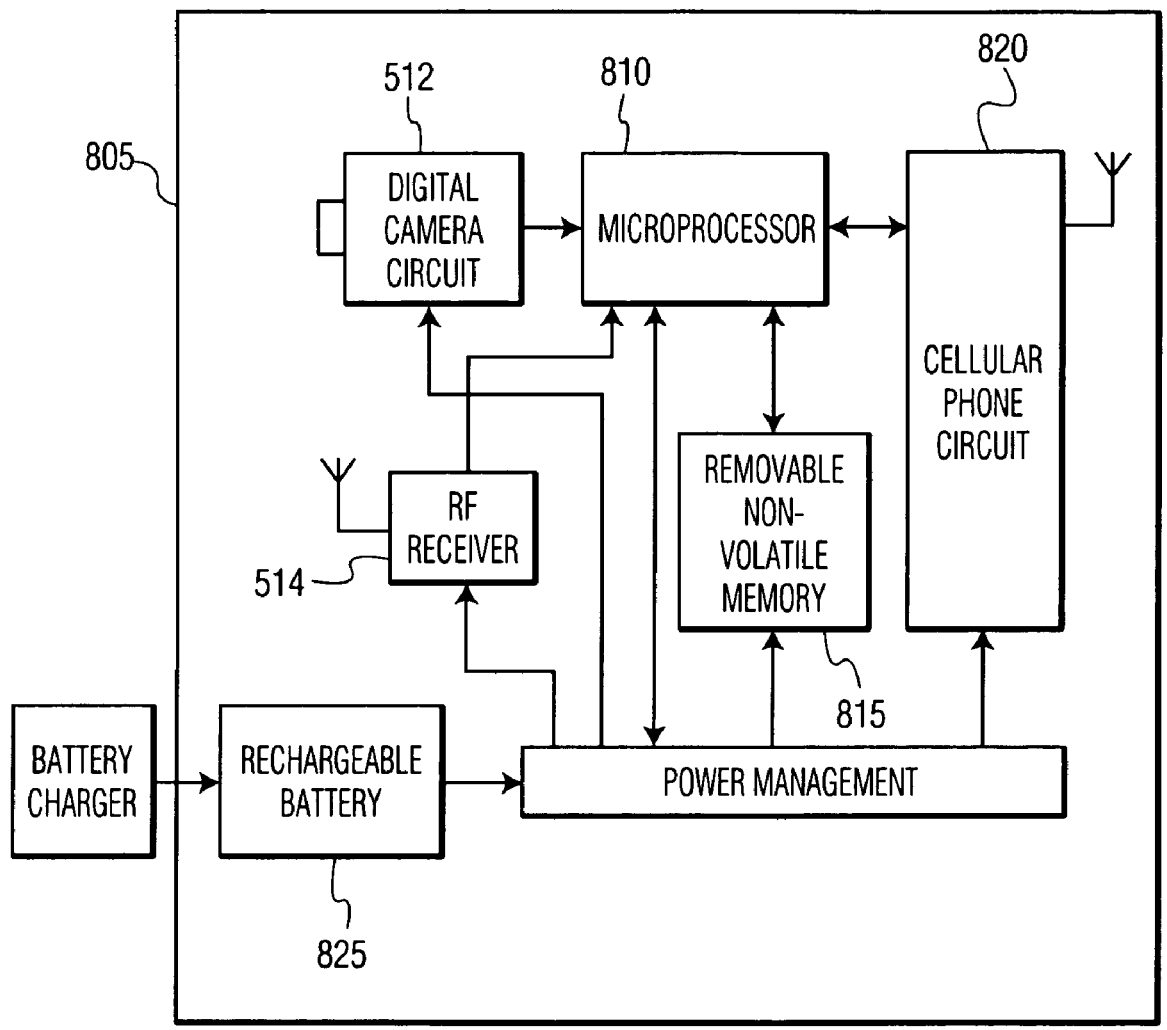
FIG. 8 shows an exemplary embodiment of an architecture of a video camera unit according to the present invention.

As shown in FIG. 8, a video camera unit 510 according to an exemplary embodiment of the present invention resides in a wearable housing 805 which may be, for example, an earpiece, a headband, a cap, etc. The housing 805 may include a microprocessor 810 for activating the video camera 512 upon receipt of the activation signal via the receiver 514. When the video camera 512 is activated, the microprocessor 810 may write video data obtained by the video camera 512 to a memory 815 (e.g., a removable, non-volatile memory) and download the video data to a wireless communication device (e.g., mobile phone, PDA, laptop, tablet, handheld computer, network interface card, etc.) via a wireless communication circuit (e.g., a cellular phone circuit 820). Alternatively, upon seizure detection or prediction, the microprocessor 810 may instruct the cellular phone circuit 820 to transmit warning signals to a remote communication device, such as the computing device 15. The video camera unit 510 may be powered by a battery 825 which is recharged when coupled to a charging device, as described below.

Figure 9:
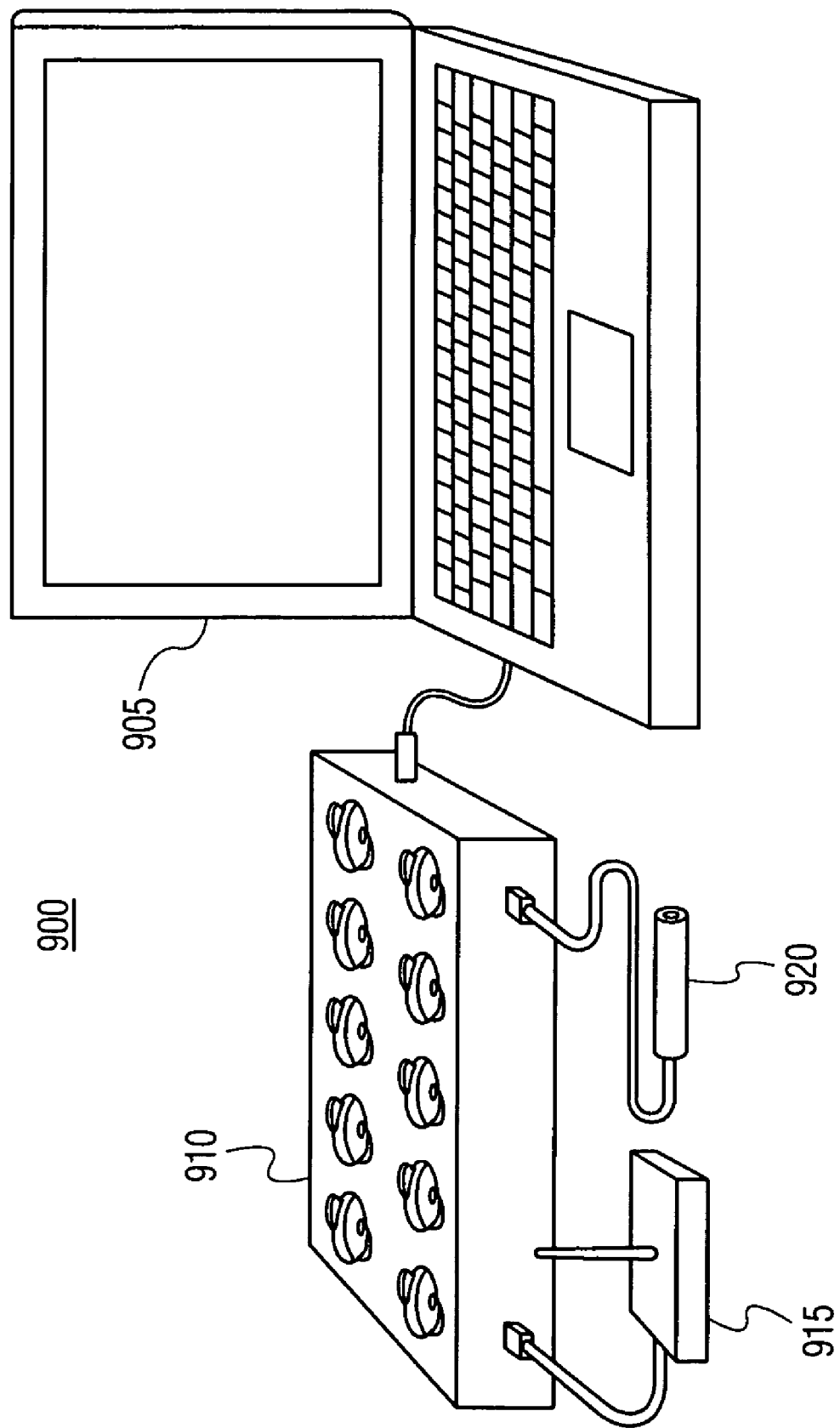
FIG. 9 shows an exemplary embodiment of a charger/data reader system according to the present invention.

As shown in FIG. 9, a charger/data reader system 900 according to an exemplary embodiment of the present invention may include a computing device 905 (e.g., a laptop, PC, tablet, etc.) coupled to a multiport charger and data reader (MCDR) 910. While the MCDR 910 may be used for charging a plurality of EEG minidiscs 505 and/or video camera units 510 simultaneously, those of skill in the art will understand that the MCDR 910 may only accommodate one or a preselected number of EEG minidiscs 505 and/or video camera units 510. In the exemplary embodiment, the MCDR 910 includes a plurality of charging ports for receiving the EEG minidiscs 505. When the EEG minidisc 505 is coupled to a charging port on the MCDR 910, the battery charging circuit 540 receives power from the MCDR 910 and charges the battery 535. When the video camera unit 510 is coupled to a charging port on the MCDR 910, the battery 825 may receive power from the MCDR 910.

When the EEG minidiscs 505 are coupled to the MCDR 910, the EEG data and the video data may be downloaded from the memory 720 and/or the memory 815 for subsequent uploading to the computing device 905. The MCDR 910 may further include an RF receiver 915 for wirelessly downloading the EEG data and/or the video data from the EEG minidisc 505 or the cellular phone circuit 820. In addition, the MCDR 910 may also be equipped with an optical transmitter 920 for activating the EEG minidisc 505 via the optical transceiver 545 of the EEG minidisc. The computing device 905 may utilize EEG processing algorithms and/or image processing algorithms to analyze the epileptic events suffered by the subject.

The present invention has been described with the reference to the above exemplary embodiments. Accordingly, various modifications and changes may be made to the embodiments without departing from the broadest spirit and scope of the present invention as set forth in the claims that follow. The specification and drawings, accordingly, should be regarded in an illustrative rather than restrictive sense.

What is claimed is:

1. A device, comprising:
   a head mounting arrangement sized and shaped to be worn on a user's head;
   a plurality of electrodes disposed on the arrangement so that, when the arrangement is worn on the user's head, the electrodes contact target portions of a scalp to detect electrical activity of a brain of the user;
   an image capture device disposed on the arrangement so that, when the arrangement is worn on the user's head, a field of view of the image capture device includes a portion of an anatomy of the user; and
   a processing unit generating EEG data from the electrical activity,
   wherein, when the EEG data is indicative of an epileptic event, the processing unit activates the image capture device to capture video data of the user.

2. The device according to claim 1, wherein the arrangement is one of a headband and a cap.

3. The device according to claim 1, wherein the electrodes include at least four electrodes disposed in a predetermined configuration on the arrangement.

4. The device according to claim 1, wherein each of the electrodes is contained in an electrode unit, the electrode unit further comprising an operational amplifier coupled directly to the corresponding electrode.

5. The device according to claim 4, wherein the electrode unit further comprises:
   an adhesive delivery arrangement securing the electrode unit to the scalp; and
   a conductive paste delivery arrangement applying a conductive paste to electrically couple the electrode to the scalp.

6. The device according to claim 1, wherein the image capture device is one of a video camera and a digital camera.

7. The device according to claim 1, wherein the field of view of the image capture device includes one of trunk, hands and feet of the user.

8. The device according to claim 1, further comprising:
   a memory,
   wherein the processing unit writes at least a portion of one of the EEG data and the video data to the memory.

9. The device according to claim 8, wherein the memory is a removable memory device.

10. The device according to claim 8, wherein the memory includes reference data corresponding to EEG data obtained from one of the subject and a group of subjects.

11. The device according to claim 10, wherein the processing unit compares the EEG data to the reference data to determine if the user is experiencing the epileptic event.

12. The device according to claim 11, wherein the epileptic event is a seizure.

13. The device according to claim 11, wherein the epileptic event is brain activity preceding a seizure.

14. The device according to claim 1, further comprising:
   an indicator activated upon detection of the epileptic event.

15. The device according to claim 14, wherein the indicator is one of a light-emitting diode and a speaker.

16. The device according to claim 1, further comprising:
   a wireless transceiver transmitting a warning signal upon detection of the epileptic event to one of a remote display device and a remote computing device.

17. The device according to claim 16, wherein the warning signal includes at least one of (i) identification data identifying the user, (ii) medical history data corresponding to a medical history of the user, (iii) location data indicative of a location of the user, (iv) the EEG data and (v) the video data.

18. The system according to claim 17, wherein the electrode unit further comprises:
   a rechargeable battery supplying power to the processing unit, the electrodes and the wireless transmitter.

19. The system according to claim 17, wherein the processing unit transmits a warning signal upon detection of the epileptic event.

20. The device according to claim 1, further comprising:
   a rechargeable battery supplying power to the processing unit, the electrodes, the image capture device and the transceiver.

21. A system, comprising:
   an electrode unit attached to a scalp of a subject, the electrode unit comprising:
      a plurality of electrodes generating electrical signals corresponding to electrical activity of a brain of the subject;
      a processing unit generating EEG data from the electrical signals; and
      a wireless transmitter,
   an image capture unit worn on a head of the subject, the image capture unit comprising:
      an image capture device; and
      a wireless receiver,
   wherein, when the EEG data is indicative of an epileptic event, the processing unit transmits an activation signal to the image capture unit via the wireless transmitter to activate the image capture device to capture video data of the subject.

22. A system, comprising:
   a wireless computing device; and
   a head wearable arrangement comprising:
      a plurality of electrodes disposed on the arrangement so that, when the arrangement is worn on a head in a desired orientation, the electrodes contact target portions of a scalp of the subject to generate electrical signals corresponding to electrical activity of a brain of the subject;
      an image capture device disposed on the arrangement, the image capture device capture video data of the subject;
      a wireless transceiver; and
      a processing unit generating EEG data from the electrical signals,
   wherein, when the EEG data is indicative of an epileptic event, the processing unit downloads the EEG data and the video data to the wireless computing device via the wireless transceiver.

* * * * *